United States Patent [19]
Fritzsch

[11] Patent Number: 5,542,945
[45] Date of Patent: Aug. 6, 1996

[54] ELECTRO-SURGICAL RADIO-FREQUENCY INSTRUMENT

[75] Inventor: Gernod Fritzsch, Tuttlingen, Germany

[73] Assignee: Delma elektro-u. medizinische Apparatebau Gesellschaft mbH, Tuttlingen, Germany

[21] Appl. No.: 304,075

[22] Filed: Sep. 12, 1994

[30] Foreign Application Priority Data

Oct. 5, 1993 [DE] Germany ............. 43 33 983.2

[51] Int. Cl.⁶ ................................. A61B 17/36
[52] U.S. Cl. ................. 606/48; 606/41; 606/50; 128/642
[58] Field of Search .............. 606/41, 42, 45, 606/50, 48, 28–34, 37–42, 45–50; 128/642

[56] References Cited

U.S. PATENT DOCUMENTS

| | | | |
|---|---|---|---|
| 2,100,116 | 11/1937 | Webb | 606/50 |
| 2,249,894 | 7/1941 | Goldstein | 606/50 X |
| 4,043,342 | 8/1977 | Morrison, Jr. | 606/50 X |
| 4,823,791 | 4/1989 | D'Amelio et al. | 606/50 X |
| 4,862,890 | 9/1989 | Stasz . | |
| 5,071,418 | 12/1991 | Rosenbaum | 606/42 |
| 5,080,660 | 1/1992 | Buelna | 606/49 |
| 5,116,333 | 5/1992 | Beane | 606/42 X |
| 5,267,994 | 12/1993 | Gentelia et al. | 606/41 |
| 5,281,216 | 1/1994 | Klicer | 606/50 X |

FOREIGN PATENT DOCUMENTS

| | | | |
|---|---|---|---|
| 3245570 | 6/1984 | Germany | 606/50 |
| 4113037A1 | 10/1992 | Germany . | |

Primary Examiner—Angela D. Sykes
Assistant Examiner—Michael Peffley
Attorney, Agent, or Firm—Townsend and Townsend and Crew

[57] ABSTRACT

An electro-surgical radio-frequency instrument is described for the coagulating and/or cutting of tissue with a shaft having a radio-frequency voltage connection. A working tip is arranged at the distal end of the shaft and has two electrodes which are connected or connectable to a radio-frequency voltage connection. The working tip is shaped as a hook or a spatula and comprises the two electrodes which are arranged next to one another, and an insulation layer which is arranged between them and which is connected to the electrodes so as to form a unit.

19 Claims, 3 Drawing Sheets

ELECTRO-SURGICAL RADIO-FREQUENCY INSTRUMENT

BACKGROUND OF THE INVENTION

The invention relates to an electro-surgical radio-frequency instrument for coagulating and/or cutting tissue.

Such electro-surgical RF-instruments are often used for laparoscopic operations, where it is important that the working tip and the shaft should be formed as narrowly as possible. By changing the RF-voltage which energizes the electrodes, the operating mode of the RF-instrument can be switched between coagulating and cutting of the treated tissue.

Known monopolar instruments which follow customary medical instruments are usually hook-shaped or spatula-shaped, so that they are easy to operate and their handling is familiar to most surgeons. The bipolar instruments however usually have opposing movably journalled electrodes, with which in addition to the coagulating or the cutting, a clamping of the tissue can be effected.

Since the use of monopolar instruments, for example in the abdomen, involves safety risks for the patient and the surgeon, safety-conscious surgeons use only bipolar RF-instruments there.

The existing bipolar electro-surgical instruments however are complicated, costly, and sensitive, so that in comparison to the known monopolar instruments their use requires particular dexterity by the surgeon. Furthermore, most of the known bipolar instruments become soiled very quickly and are difficult to clean.

SUMMARY OF THE INVENTION

It is therefore an object of the invention to provide a bipolar electro-surgical radio-frequency instrument for the coagulating and/or cutting of tissue, which is constructed and can be operated in a simple manner, offers maximum safety for the patient and the surgeon, is simple to clean and to sterilize, is particularly suited for laparoscopic examinations, and is universally suited for mechanical-surgical and/or electro-surgical operations.

Tissue can universally mechanically be acted on by the hook-shaped or spatula-shaped form of the working tip in the manner characteristic for hooks and spatulae, wherein an electro-surgical coagulating process and/or cutting process can at the same time be initiated in a spatially tightly bounded region around the working tip. Since the working tip, independent from its form as a modular unit comprising two electrodes and one insulation layer, can be formed to be as compact and narrow as a spatula or hook which operates in a purely mechanical manner, the instrument of the invention is especially suited for spatially limited conditions such as arise for example during laparoscopic operations.

The uniform and robust form of the RF-instrument makes a simple handling and easy cleaning possible. For example, through simple rearward hooking behind the tissue to be treated, the tissue can be cut by applying an RF-voltage which is suitable for the cutting process or can be coagulated by applying a voltage which is suitable for the coagulation by placement of the hook curvature onto the tissue which is to be treated. At the same time, the required safety for the patient and for the surgeon is ensured by the construction as a bipolar RF-instrument.

According to a preferred embodiment of the invention, at least one of the electrodes is tapered in the region of the free end of the working tip and/or partly covered by an insulation material. As a result, the current density which exists during the current transfer from the electrode to the tissue is increased in this region of the working tip, so that the tapered and/or covered region of the working tip is especially well suited for the cutting process. In particular, the taper can extend from approximately the center of the curvature of the hook to the free end of the hook, while the electrodes in the remaining region of the hook have a relatively wide cross-sectional surface, in particular in the radially outwardly disposed region of the curvature which is arranged away from the free end of the hook. In this way, the cutting property of one half of the hook, for example during the hooking behind the tissue, as well as the coagulating property of the other half of the hook can be improved further. Preferably, both electrodes are formed in a tapered or covered manner, so that the working tip has a symmetrical shape.

In accordance with a further preferred embodiment of the invention, the working tip, or a base body which carries it, is releasably attached to the elongated shaft. Thus, working tips with different shapes can be attached to one and the same shaft, whereby the application possibilities of an embodiment of the instrument in accordance with the invention can be increased further. An additional advantage is that the tips which become very soiled during the operation can be treated as a disposable product. This decreases the time and effort involved in cleaning and the hygiene improves.

Preferably, the working tip, or a base body which carries it, is attached to the shaft via one or several latch elements, whereby a simple and quick release of the working tip is ensured. However, attachments to the shaft by directly screwing the working tip to it or by a sleeve nut or by a bayonet catch are conceivable.

The invention will now be described in the following by way of example and with reference to the drawings.

DESCRIPTION OF THE PREFERRED EMBODIMENTS

Figure 1:
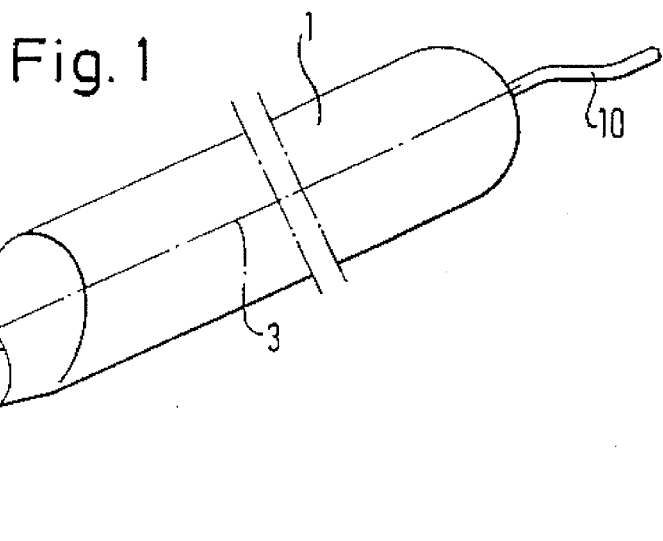
FIG. 1 is a schematic, perspective partial view of an embodiment of the RF-instrument made in accordance with the invention.
Figure 2:
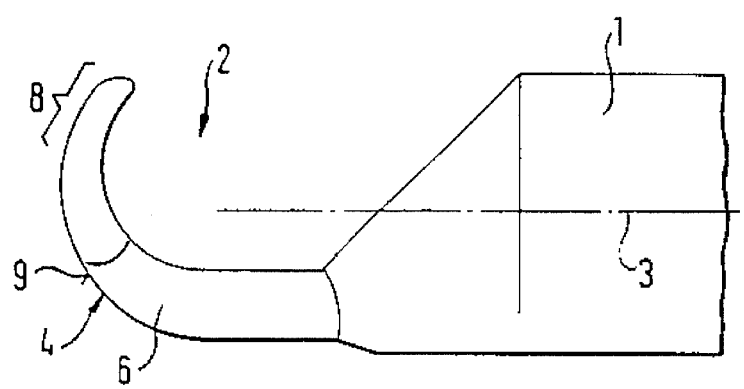
FIG. 2 is a side view of the RF-instrument shown in Fig 1.

The electro-surgical RF-instrument shown in FIGS. 1 and 2 comprises a shaft 1 which takes up the supply of current and which at the same time serves as a handle. At the distal end of the shaft 1, a working tip 2 is arranged, the front end of which initially extends in the direction of the longitudinal axis 3 of the shaft 1 and is then upwardly bent to form a hook 4.

The working tip 2 is constructed in layers, wherein the two outer layers are made of metal and each forms an electrode 5, 6 with an insulation layer 7 being provided between them. The insulation layer 7 fills in the entire intermediate space between the electrodes 5, 6, wherein the points of transition at the surface of the working tip 2 between the electrodes 5, 6 and the insulation layer 7 are formed in a continuously extending manner, so that the combined thicknesses of the electrodes and the insulating layer form a continuous and interruption-free side surface of the tip. This side surface is shaped, for example, as part of a hook or a spatula defined by the working tip, so that it can be used for mechanically surgically working on the tissue while a potential applied to the electrodes can be used to coagulate tissue.

In the region of the free end 8 of the working tip 2, the electrodes 5, 6 are tapered in comparison to the region of the forwardly curvature 9 of the hook 4.

At the rearward end of the shaft 1, a cable 10 is provided which connects the RF-instrument to an electro-surgical radio-frequency generator which is not shown.

Figure 3:
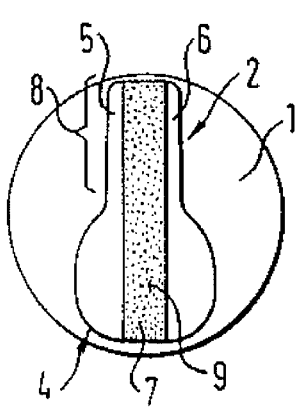
FIG. 3 is a front view of the RF-instrument shown in FIG. 1.

In the front view according to FIG. 3, the tapering of the electrodes 5, 6 at all sides in the region of the free end 8 of the working tip 2 can be seen. It extends from approximately the middle of the curvature 9 of the hook 4 up to the free end 8 of the working tip 2. In the remaining region of the working tip 2, the electrodes 5, 6 are sufficiently wide so that an approximately circular cross-section results. It is important that the hook 4 is formed and arranged in such a manner that it does not anywhere laterally project from the shaft 1.

Figure 4:
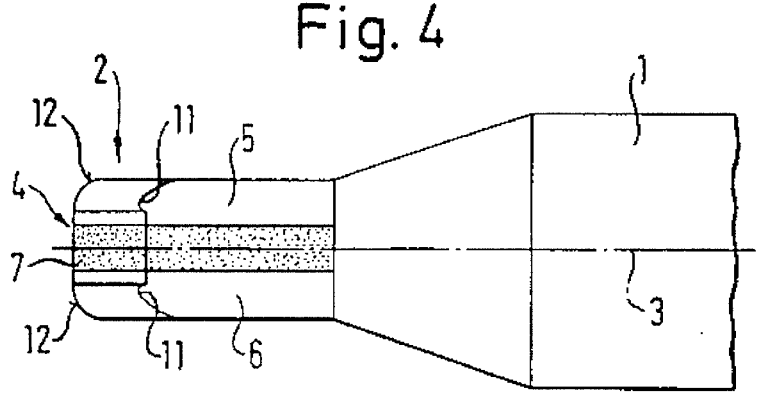
FIG. 4 is a plan view of the RF-instrument shown in FIG. 1.

FIG. 4 shows the symmetrical arrangement of the working tip 2 and thus of the electrodes 5, 6 relative to the longitudinal axis 3 of the shaft 1. The working tip 2 however can also be attached laterally displaced from the longitudinal axis 3, if this, for example, leads to an improved handling of the instrument or in a clearer view of the operation site. In contrast to the radially inwardly disposed edges 11, the edges 12 in the outward region of the hook 4 are formed in a rounded manner.

The manner of operation of the electro-surgical RF-instrument in accordance with FIGS. 1 to 4 will be described in more detail in the following:

An RF-voltage suitable for the coagulating or for the cutting is supplied via the cable 10 as required to the electro-surgical RF-instrument which has been inserted through a trocar into the interior of the body. The switching on of the RF-voltage can for example be realized by a switch which is not shown, in particular by a finger key at the shaft 1, a foot switch, such as a pedal, or directly at the radio-frequency generator.

For coagulation, preferably the forwardly disposed region of the curvature 9 of the hook 4 is placed on the tissue which is to be coagulated, so that the electrodes 5, 6 which are relatively wide in this region come into contact with the tissue. Due to the continuous transitions in the surface region of the working tip 2 between the electrodes 5, 6 and the insulation layer 7, as well as due to the rounded edges 12, a perfect gliding on the tissue surface is possible, so that injuries caused by the displacement of the instrument along the tissue as well as the hooking of the working tip 2 into the tissue are prevented.

For cutting, the hook 4 is preferably guided behind the tissue which is to be cut, so that the tissue contacts the inner side of the hook 4 in the region of the tapered electrodes 5, 6. Due to the higher current density at the current transition from the electrodes 5, 6 to the tissue in the region of the tapered electrodes 5, 6, the tissue cells are exploded so that the tissue is cut by simply pulling the instrument back.

Figure 5:
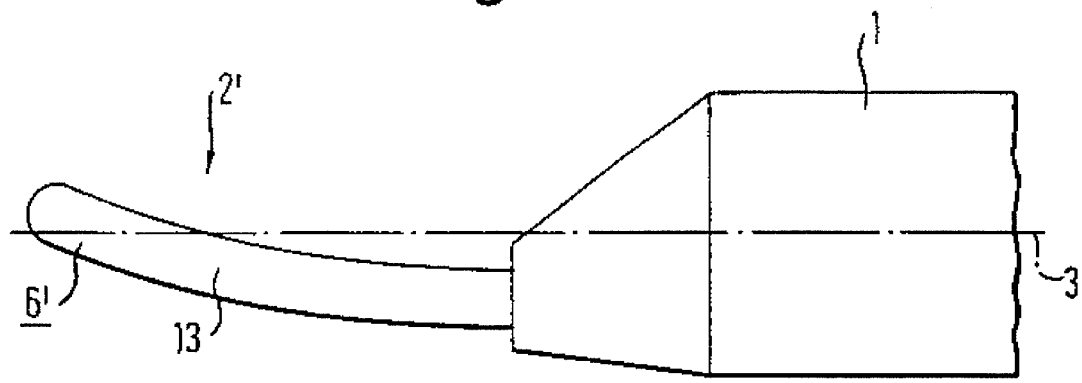
FIG. 5 is a partial side view of a further embodiment of the invention, FIG. 6. is a plan view of the embodiment shown in FIG. 5.
Figure 6:
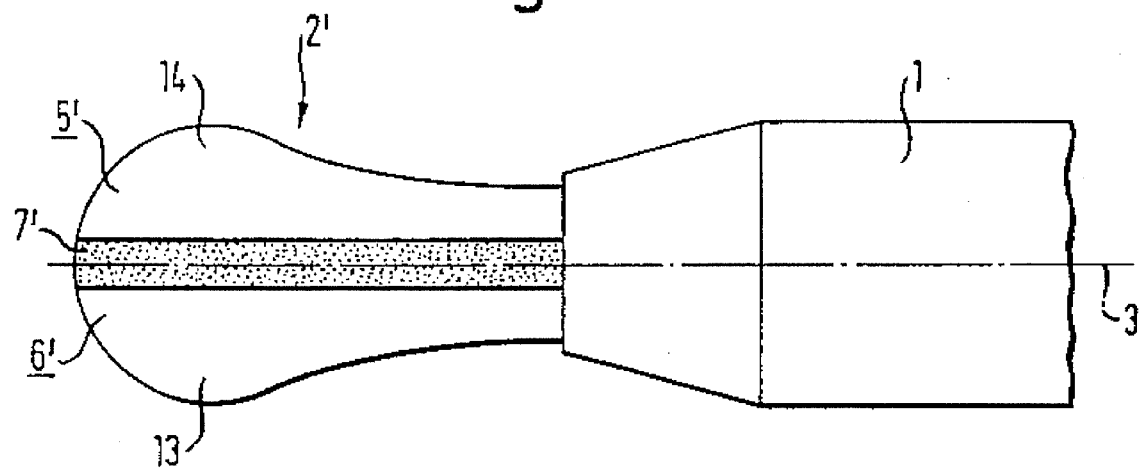

The FIGS. 5 and 6 show an embodiment according to the invention in the form of an electro-surgical RF-instrument with a spatula-shaped and only slightly bent working tip 2'. While the width of the insulation layer 7' shown in FIG. 6 substantially corresponds to the width of the hook-shaped working tip 2, the electrodes 5', 6' each have distinctive enlargements 13, 14 at their front regions.

Due to the spatula-shaped form of the working tip 2', a particularly good large-area coagulation of tissue is possible, with the rounded contours of the working tip 2' ensuring a gentle treatment of the tissue.

Figure 7:
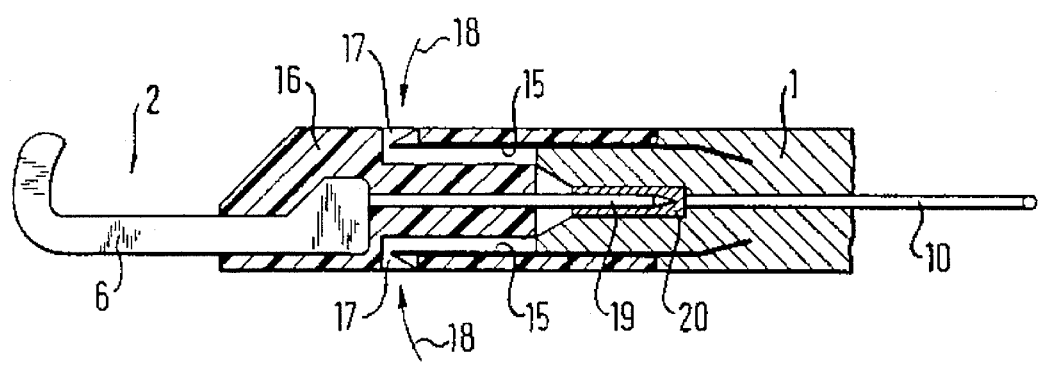
FIG. 7 is a schematic longitudinal section through a further embodiment of the invention and, FIG. 8 is a schematic longitudinal section through another embodiment of the invention.

In the longitudinal section of an embodiment of the invention shown in FIG. 7, the working tip 2 is connected to the shaft 1 via latch elements 15 on shaft 1. The working tip 2 is secured in an insulating base body 16 which has latch recesses 17 engaged by latch elements 15. By pressing in the latch elements 15 in direction of the arrows 18, the base body 16 and thus working tip 2 can be decoupled from the shaft 1.

At its end adjacent to shaft 1, the working tip 2 further comprises two contact pins 19 of which only one is shown due to the sectional view in FIG. 7. The contact pins 19 are each connected to the electrode 5 or 6 and, in the assembled instrument, establish the electric connection between the working tip 2 and the cable 10 via contact sockets 20 (of which also only one is shown) which are provided in the shaft 1 and thus form a connection to the radio-frequency generator. Due to the plug connection of the electrical connections, combined with the simultaneous mechanical latch connection of the working tip 2 or the base body 16 to the shaft 1, different working tips 2 can be simply and quickly, exchanged even during an operation.

The electrical connection can however for example be also established directly by metallic latch elements which are made to be insulating towards the surface of the shaft 1. In this way, the electrical and the mechanical connection coincide due to the double function of the latch elements.

Figure 8:
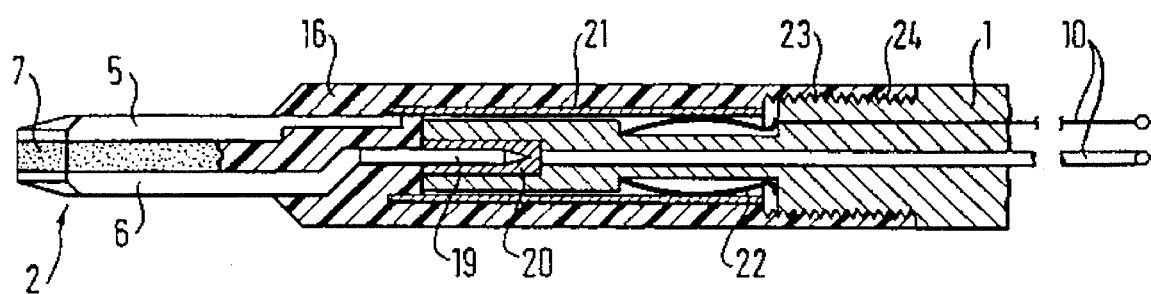

FIG. 8 shows a further embodiment of the invention, in which the working tip 2 is screwed to the shaft 1, via base body 16. At its end which faces the shaft the base body 16 has an internal screw thread 23 which can be screwed to an external screw thread 24 provided on shaft 1.

The electrical connection of the one electrode 6 to the radio-frequency generator is established as shown in FIG. 7 by a contact pin 19 which is arranged in a contact socket 20. The other electrode 5 is connected to a contact tube 21 which is arranged coaxially with the longitudinal axis 3 of the shaft. Sliding contacts 22 are arranged within the contact tube 21 in such a way as to engage with the interior side of the contact tube 21 and thus establish the electrical connection between the electrodes 5, 6 of the working tip 2 and the radio-frequency generator. An unproblematic screwing together or unscrewing of the base body 16 and the shaft 1 is ensured by forming the electrical connection by means of sliding contacts 22 within the coaxially arranged contact tube 21.

Apart from the connection methods described, any suitable releasable means for connection of the working tip 2 to the shaft 1 is conceivable, such as for example sleeve nuts, bayonet connections, plug connections or other snap connections.

What is claimed is:

1. A bipolar electro-surgical radio-frequency instrument for the coagulating and/or cutting of tissue comprising: a shaft; a work tip attached to the shaft including a flat elongated insulating layer having first and second parallel plane surfaces of equal size and shape, and first and second electrodes of equal size and mirror-symmetrical shape each having a plane surface which is parallel with and of the same size as the first and second plane surfaces, respectively, of the flat insulating layer, and being attached thereto so that a transition from the plane surfaces of the electrodes to the first and second surfaces of the insulating layer is smooth and continuous, the insulating layer and the first and second electrodes forming a unit which is shaped to form a hook having an axis of curvature which is substantially perpendicular to the first and second plane surfaces of the insulating layer; and means for connecting the electrodes to a radio frequency voltage.

2. A bipolar electro-surgical instrument in accordance with claim 1 wherein at least one of the electrodes is tapered in a region of the hook forming a free end of the hook.

3. A bipolar electro-surgical instrument according to claim 1 wherein at least one of the electrodes is partly covered by an insulation material.

4. A bipolar electro-surgical instrument in accordance with claim 3 wherein exposed sides of the electrodes are tapered in the region of the free end of the hook from approximately a middle of the curvature of the hook to the free end thereof.

5. A bipolar electro-surgical instrument in accordance with claim 4 wherein a portion of the working tip adjoining the hook is relatively wider and has an approximately circular cross-section.

6. A bipolar electro-surgical instrument in accordance with claim 1 wherein the hook includes relatively sharp radially inwardly oriented inner edges and relatively rounded, radially outwardly directed outer edges.

7. A bipolar electro-surgical instrument in accordance with claim 1 wherein the electrodes include exterior surfaces which are at least substantially parallel to the plane surfaces of the insulating layer from the shaft to a beginning of a curvature defining the hook.

8. A bipolar electro-surgical instrument in accordance with claim 1 wherein a curvature of the hook extends over an arc of more than 90°.

9. A bipolar electro-surgical instrument in accordance with claim 1 including means for releasably attaching the working tip to the shaft.

10. A bipolar electro-surgical instrument in accordance with claim 9 wherein the attaching means comprises at least one latch element.

11. A bipolar electro-surgical instrument in accordance with claim 9 wherein the radio-frequency connection is located at an interface between the shaft and the working tip and comprises at least one of a voltage plug contact and a voltage sliding contact at the interface.

12. A bipolar electro-surgical radio-frequency instrument for the coagulating and/or cutting of tissue comprising: a shaft having a longitudinal axis; a working tip adapted to be attached to the shaft so that it extends substantially parallel to the longitudinal axis away from the shaft, the tip including a flat elongated insulating layer having first and second parallel, plane surfaces of equal size and shape extending away from the shaft, and first and second electrodes of equal size and mirror-symmetrical shape each having one plane surface which is parallel with and of the same size as the first and second plane surfaces, respectively, of the flat insulating layer, and being attached thereto so that the transition from the plane surfaces of the electrodes to the first and second surfaces of the insulating layer is continuous and interruption-free, the insulating layer being shaped as a rod with a rectangular section and the electrodes having a symmetrical blade-like shape and a rounded lateral extension proximate an end of the tip remote from the shaft to thereby form a spatula-shaped unit comprising the insulating layer and the first and second electrodes; and means for connecting the electrodes to a radio frequency voltage.

13. A bipolar electro-surgical instrument in accordance with claim 12 wherein the insulating layer and the electrodes have a relatively slight curvature about an axis and with a radius which both are substantially perpendicular to the longitudinal axis of the shaft.

14. A bipolar electro-surgical instrument in accordance with claim 13 including means for releasably attaching the working tip to the shaft.

15. A bipolar electro-surgical instrument in accordance with claim 14 wherein the attaching means comprises at least one latch element securing the working tip to the shaft.

16. A bipolar electro-surgical instrument in accordance with claim 15 wherein the working tip includes a base body adapted to be attached to the shaft, and wherein the latch element secures the base body to the shaft.

17. A bipolar electro-surgical instrument in accordance with claim 14 wherein the radio-frequency connection is located at an interface between the shaft and the working tip and comprises at least one of a voltage plug contact and a voltage sliding contact at the interface.

18. A bipolar electro-surgical radio-frequency instrument for coagulating and/or mechanically surgically working on tissue, the instrument comprising: a shaft having a longitudinal axis, a radio-frequency voltage connection and a working tip attached to and extending substantially in the direction of the longitudinal axis away from the shaft, the tip including a flat elongated insulating layer having first and second parallel, plane surfaces of a given size and shape extending away from the shaft, and first and second electrodes of equal size and mirror-symmetrical shape each having one plane surface which is parallel with, of the same size as and abuts the first and second plane surfaces, respectively, of the flat insulating layer, peripheral surfaces of the insulating layer and the electrodes forming a continuous and interruption-free side surface of the working tip which extends transversely to the longitudinal axis from an exterior side of the first electrode facing away from the insulating layer to an exterior side of the second electrode facing away from the insulating layer so that the insulating layer is sandwiched between the electrodes, the electrodes and the insulating layer being shaped to define the working tip in the form of a mechanical-surgical instrument capable of coagulating the tissue and mechanically surgically working on the tissue.

19. Medical instrument for treating tissue during medical operations and adapted to be used as a bipolar electro-surgical radio-frequency instrument for coagulating and/or cutting the tissue, the instrument comprising: a shaft; a working tip connected with the shaft and shaped in the form of one of a hook and a spatula for treating the tissue during medical operations, the working tip simultaneously defining the instrument for coagulating and/or cutting the tissue and for that purpose including a flat elongated insulating layer having first and second plane surfaces of equal size and shape, a spacing between the first and second surfaces being identical over their entire extent, first and second electrodes of equal size and mirror-symmetrical shape each having a plane surface which is parallel with, of the same size as and abuts the first and second plane surfaces, respectively, of the flat insulating layer so that the insulating layer is sandwiched between the electrodes, and so that a peripheral surface of the instrument defined by peripheries of the electrodes and the insulating layer is smooth and continuous, exterior surfaces of the first and second electrodes having portions adapted to be brought into direct contact with the tissue, and means for connecting the electrodes to a radio-frequency voltage.

* * * * *